United States Patent [19]

Aramaki et al.

[11] Patent Number: 4,925,975

[45] Date of Patent: May 15, 1990

[54] METHOD OF PREPARING ALKALI METAL FLUOROALKYLSULFONATES OF HIGH PURITY

[75] Inventors: Minoru Aramaki; Kimitaka Okamoto; Hiroaki Sakaguchi; Tamio Nakamura, all of Yamaguchi, Japan

[73] Assignee: Central Glass Company, Limited, Ube, Japan

[21] Appl. No.: 342,348

[22] Filed: Apr. 21, 1989

[30] Foreign Application Priority Data

Apr. 21, 1988 [JP] Japan ................................. 63-96820

[51] Int. Cl.$^5$ ........................................... C07C 143/02
[52] U.S. Cl. .................................. 562/113; 562/115; 562/124
[58] Field of Search ..................... 562/113, 115, 124

[56] References Cited

FOREIGN PATENT DOCUMENTS 7405112 10/1974 Netherlands ........................ 562/113

Primary Examiner—Alan Siegel
Attorney, Agent, or Firm—Fleit, Jacobson, Cohn, Price, Holman & Stern

[57] ABSTRACT

In preparing a fluoroalkylsulfonate $RfSO_3M$, where Rf is a perfluoroalkyl gruop having not more than 6 carbon atoms and M is an alkali metal, by neutralization reaction between a fluoroalkylsulfonic acid $RfSO_3H$ and an alkali metal carbonate or hydroxide, the reaction is carried out under acidic conditions such that at the end of the reaction pH of the reaction liquid is lower than 6, and preferably not higher than 3. By so maintaining the reaction liquid acidic, the obtained $RfSO_3M$ becomes very low in the concentrations of anionic impurities such as free fluorine, free chlorine and carbonate radical and, besides becomes low in moisture absorbency.

5 Claims, No Drawings

METHOD OF PREPARING ALKALI METAL FLUOROALKYLSULFONATES OF HIGH PURITY

BACKGROUND OF THE INVENTION

This invention relates to the preparation of alkali metal perfluoroalkylsulfonates by the reaction between a perfluoroalkylsulfonic acid and an inorganic alkali metal compound, and more particularly to an improved method using the same reaction for obtaining alkali metal perfluoroalkylsulfonates high in purity and very low in the concentrations of anionic impurities.

Alkali metal salts of perfluoroalkylsulfonic acids are useful as supporting electrolytes in electric cells or as catalysts for organic synthesizing reactions and polymerization reactions.

Alkali metal perfluoroalkylsulfonates are generally prepared by a neutralization reaction between a perfluoroalkylsulfonic acid and an alkali metal carbonate or hydroxide. For obtaining a high purity product by this reaction it is essential to use refined reactants. When care is taken in this regard the reaction product is very low in the concentrations of cationic impurities such as sodium, calcium, silicon, iron, lead, etc. even though the neutralization reaction is carried out in an ordinary manner and followed by simple washing and drying of the reaction product.

However, industrially refined perfluoroalkylsulfonic acids and alkali metal compounds usually contain uneligible amounts of anionic impurities such as free chlorine and free fluorine, and most of these anionic impurities remain in the product of the neutralization reaction carried out in the usual manner.

In another aspect, alkali metal perfluoroalkylsulfonates prepared by the conventional method are relatively high in moisture absorbency, and hence strict restrictions are placed on the handling of the sulfonates used for electric cells or other purposes to which moisture is detrimental.

SUMMARY OF THE INVENTION

It is an object of the invention to provide a method for easily preparing alkali metal perfluoroalkylsulfonates low in the concentrations of impurities including anionic impurities and low in moisture absorbency.

The present invention provides an improved method of preparing a perfluoroalkylsulfonate represented by the general formula $RfSO_3M$, where Rf is a perfluoroalkyl group having not more than 6 carbon atoms and M is an alkali metal, by reacting in liquid phase a perfluoroalkylsulfonic acid represented by the general formula $RfSO_3H$, where Rf is as defined above, with carbonate or hydroxide of the alkali metal M. According to the invention, in carrying out the reaction between the perfluoroalkylsulfonic acid and the alkali metal carbonate o hydroxide the reaction liquid is maintained acidic such that at the end of the reaction pH of the reaction liquid is lower than 6.

With respect to the reaction between a perfluoroalkylsulfonic acid $RfSO_3H$ and an alkali metal compound $M_2CO_3$ or MOH, unexpectedly we have discovered that the concentrations of anionic impurities such as free chlorine, free fluorine and carbonate radical in the aimed reaction product $RfSO_3M$ remarkably decrease as pH of the reaction liquid at the end of the reaction is shifted from the neutral level toward the acidic side.

That is, according to the invention very low concentrations of anionic impurities can be attained by simply controlling the pH condition of the reaction liquid without relying on any special treatment of the reaction product other than usual drying by heating. Of course the perfluoroalkylsulfonates obtained by the method according to the invention are low in the concentrations of cationic impurities insofar as the starting materials are refined as usual in the conventional method using the same neutralization reaction.

Preferably the reaction is carried out such that at the end of the reaction pH of the reaction liquid is not higher than 3.

Presumably the following are the reasons for the decrease in the concentrations of anionic impurities in the product of the reaction according to the invention. Since the reaction is carried out under acidic conditions bubbling of carbon dioxide gas will occur in the reaction liquid, and hence fluorine and chlorine probably existing in the form of HF and HCl will be carried away from the reaction liquid by the carbon dioxide gas. During the reaction under acidic conditions carbonate radical will decompose into carbon dioxide gas, and the gas will readily leave the reaction liquid. Furthermore, since the reaction product is in an acidic state heating of the product for drying will cause the anionic impurities to dissipate as HF, HCl and $H_2CO_3$.

Another important merit of the invention is that the obtained perfluoroalkylsulfonates are low in moisture absorbency. When the same sulfonates are prepared by carrying out the neutralization reaction under neutral or nearly neutral conditions such that pH of the reaction liquid becomes 7 to 8 at the end of the reaction, the dried sulfonates soon absorb considerable moisture even in an atmosphere very low in the content of moisture such as the atmosphere in a dry box containing a strong desiccant.

The reason for the lowering of moisture absorbency has not been elucidated yet. Presumably, heating of the reaction product in an acidic state for drying may cause enhancement of chemical stability of the product by a certain mechanism.

DESCRIPTION OF THE PREFERRED EMBODIMENTS

Typical examples of perfluoroalkylsulfonic acids for use in this invention are trifluoromethylsulfonic acid and pentafluoroethylsulfonic acid.

In the practice of the invention it is suitable to select an alkali metal compound from lithium carbonate, sodium carbonate, potassium carbonate, lithium hydroxide, sodium hydroxide and potassium hydroxide.

In reacting a selected perfluoroalkylsulfonic acid, which is liquid at normal temperature, with a selected alkali metal carbonate or hydroxide it is possible to directly put the alkali metal compound in solid state into the sulfonic acid. However, it is preferred to add an aqueous solution of the alkali metal compound to an aqueous solution of the sulfonic acid, because when the alkali metal compound in solid state is directly put into the sulfonic acid it is often that the acid and the carbonate or hydroxide react too vigorously, or even violently, with unfavorable phenomena including a considerable rise in the temperature of the reaction system.

In carrying out the reaction between the sulfonic acid and the alkali metal carbonate or hydroxide the reaction liquid is maintained acidic, and it is essential that at the end of the reaction pH of the reaction liquid is lower than 6, and preferably not higher than 3. By performing the reaction in this manner the concentrations of anionic impurities such as free fluorine, free chlorine and carbonate radical in the obtained sulfonate can greatly be decreased by comparison with the case of performing the same reaction in a neutral region of pH, from 7 to 8.

In some cases the sulfonate formed by the reaction may be in the form of precipitate. If so the precipitate is separated from the mother liquor by filtration and then dried at an adequately elevated temperature. In other cases the sulfonate is partially or entirely dissolved in the reaction liquid. In such cases the sulfonate is precipitated by heating the reaction liquid to evaporate water.

The invention is further illustrated by the following nonlimitative examples.

EXAMPLE 1

A teflon vessel was charged with 75% aqueous solution of $CF_3SO_3H$ (free fluorine 10 ppm, free chlorine 7 ppm, carbonate radical less than 40 ppm), and refined $Li_2CO_3$ (free fluorine 10 ppm, free chlorine 7 ppm) was put into the solution such that the reaction between the acid and the carbonate proceeded under acidic conditions and terminated while pH of the reaction liquid was 2.

After that the reaction liquid was transferred into another teflon vessel and dried therein at 200° C. to thereby obtain a white powder of $CF_3SO_3Li$. Analysis revealed that in the obtained sulfonate powder the concentrations of impurities were remarkably lower than in the starting materials. In the sulfonate powder free fluorine was less than 1 ppm, free chlorine was less than 1 ppm, and carbonate radical was less than 40 ppm.

The obtained sulfonate powder was dried and left in a dry box containing $P_2O_5$. The content of moisture in the dried sulfonate powder was initially 160 ppm and after 1 hr still remained at 160 mm. In 25 hr the moisture content slightly increased to 210 ppm.

COMPARATIVE EXAMPLE 1

The reaction of Example 1 was repeated, using the same reaction vessel and starting materials, except that the reaction was terminated when pH of the reaction liquid was 6. Then the reaction liquid was dried in the same manner as in Example 1.

In the obtained powder of $CF_3SO_3Li$ free fluorine was 10 ppm, free chlorine was 7 ppm, and carbonate radical was 1800 ppm. That is, free fluorine and free chlorine in the starting materials almost entirely remained in the reaction product, and the product occluded a considerable amount of carbonate radical probably originated in unreacted $Li_2CO_3$.

The obtained sulfonate powder was dried and left in the dry box in the same manner as in Example 1. The content of moisture was initially 180 ppm and increased to 210 ppm in 1 hr.

EXAMPLE 2

A teflon vessel was charged with 75% aqueous solution of $CF_3SO_3H$ used in Example 1, and $K_2CO_3$ (free fluorine 31 ppm, free chlorine 18 ppm) was put into the solution such that the reaction between the acid and the carbonate proceeded under acidic conditions and terminated while pH of the reaction liquid was 2. Then the reaction liquid was dried in the same manner as in Example 1 to thereby obtain a white powder of $CF_3SO_3K$.

In the obtained sulfonate powder free fluorine was less than 1 ppm, free chlorine was less than 1 ppm, and carbonate radical was less than 40 ppm.

COMPARATIVE EXAMPLE 2

The reaction of Example 2 was repeated except that the reaction was terminated when pH of the reaction liquid was 6. The reaction liquid was dried in the same manner as in Examples 1 and 2.

In a powder of $CF_3SO_3K$ obtained in this case free fluorine was 30 ppm, free chlorine was 15 ppm, and carbonate radical was 1200 ppm.

EXAMPLE 3

A teflon vessel was charged with 75% aqueous solution of $CF_3SO_3H$ used in Example 1, and 50% aqueous solution of NaOH (free fluorine 33 ppm, free chlorine 20 ppm, carbonate radical 1.1%) was poured into the solution such that the reaction between the acid and the alkali proceeded under acidic conditions and terminated while pH of the reaction liquid was 2. Then the reaction liquid was dried in the same manner as in Example 1 to thereby obtain a powder of $CF_3SO_3Na$.

In the obtained sulfonate powder free fluorine was less than 1 ppm, free chlorine was less than 1 ppm, and carbonate radical was less than 40 ppm.

COMPARATIVE EXAMPLE 3

The reaction of Example 3 was repeated except that the reaction was terminated when pH of the reaction liquid was 6. Then the reaction liquid was dried in the same manner as in the foregoing examples.

In a powder of $CF_3SO_3Na$ obtained in this case free chlorine was 30 ppm, free chlorine was 15 ppm, and carbonate radical was 800 ppm.

What is claimed is:

1. In a method of preparing a fluoroalkylsulfonate represented by the general formula $RfSO_3M$, where Rf is an perfluoroalkyl group having not more than 8 carbon atoms and M is an alkali metal, by reacting in liquid phase a fluoroalkylsulfonic acid represented by the general formula $RfSO_3H$, where Rf is as defined above, with carbonate or hydroxide of the alkali metal M, the improvement comprising in carrying out the reaction between the fluoroalkylsulfonic acid and the alkali metal carbonate or hydroxide maintaining the reaction liquid acidic such that at the end of the reaction pH of the reaction liquid is lower than 6.

2. A method according to claim 1, wherein at the end of the reaction pH of the reaction liquid is not higher than 3.

3. A method according to claim 1, wherein each of the fluoroalkylsulfonic acid and the alkali metal carbonate or hydroxide is in the form of aqueous solution.

4. A method according to claim 1, wherein the fluoroalkylsulfonic acid is selected from the group consisting of trifluoromethylsulfonic acid and pentafluoroethylsulfonic acid.

5. A method according to claim 1, wherein said alkali metal carbonate or hydroxide is selected from the group consisting of lithium carbonate, sodium carbonate, potassium carbonate, lithium hydroxide, sodium hydroxide and potassium hydroxide.

* * * * *